(12) United States Patent
Kim et al.

(10) Patent No.: US 9,883,896 B2
(45) Date of Patent: Feb. 6, 2018

(54) JAWBONE DISTRACTION SYSTEM AND A CONTROL METHOD THEREOF CAPABLE CONTROLLING OPERATION USING A REMOTE CONTROL

(75) Inventors: Hee Jin Kim, Seoul (KR); Jong Tae Park, Seoul (KR); Kyung Seok Hu, Seoul (KR); Hyung Jun Kim, Gyeonggi-do (KR); Jung Yul Cha, Seoul (KR); Jae Gi Lee, Seoul (KR); Gyu Hag Kim, Seoul (KR)

(73) Assignees: Industry-Academic Cooperation Foundation, Yonsei University, Seoul (KR); JIWELL ELECTRONICS CO., LTD., Bucheon-si, Gyeonggi-do (KR)

( * ) Notice: Subject to any disclaimer, the term of this patent is extended or adjusted under 35 U.S.C. 154(b) by 614 days.

(21) Appl. No.: 14/112,174

(22) PCT Filed: Apr. 27, 2012

(86) PCT No.: PCT/KR2012/003306
§ 371 (c)(1),
(2), (4) Date: Sep. 12, 2014

(87) PCT Pub. No.: WO2013/162107
PCT Pub. Date: Oct. 31, 2013

(65) Prior Publication Data
US 2015/0025587 A1    Jan. 22, 2015

(51) Int. Cl.
A61B 17/80    (2006.01)
A61B 17/66    (2006.01)
A61B 17/00    (2006.01)

(52) U.S. Cl.
CPC ........ *A61B 17/8071* (2013.01); *A61B 17/663* (2013.01); *A61B 17/8004* (2013.01); *A61B 17/8057* (2013.01); *A61B 2017/00221* (2013.01); *A61B 2017/00402* (2013.01)

(58) Field of Classification Search
CPC ..................... A61B 17/663; A61B 17/8071
See application file for complete search history.

(56) References Cited

U.S. PATENT DOCUMENTS

| | | | |
|---|---|---|---|
| 5,364,396 A | 11/1994 | Robinson et al. | |
| 5,902,304 A * | 5/1999 | Walker | A61B 17/663 606/282 |
| 6,908,469 B2 | 6/2005 | Sellers et al. | |
| 2002/0040225 A1 | 4/2002 | Sellers et al. | |
| 2002/0156485 A1 | 10/2002 | Sellers et al. | |
| 2009/0192514 A1 | 7/2009 | Feinberg et al. | |

FOREIGN PATENT DOCUMENTS

KR    10-2011-0044521 A    4/2011

* cited by examiner

*Primary Examiner* — Andrew Yang
(74) *Attorney, Agent, or Firm* — Rabin & Berdo, P.C.

(57) ABSTRACT

The present invention relates to a jawbone distraction system and control method thereof, including a jawbone extension apparatus, a remote controller and a monitor, the jawbone distractor being configured to allow a horizontal shift of alveolar bone as well as performing vertical jawbone distraction, being precisely controlled in a wireless mode and configured to control a drive of the jawbone distractor through the remote controller while ascertaining a driving state by the monitor.

29 Claims, 7 Drawing Sheets

JAWBONE DISTRACTION SYSTEM AND A CONTROL METHOD THEREOF CAPABLE CONTROLLING OPERATION USING A REMOTE CONTROL

TECHNICAL FIELD

The present invention relates to a jawbone distraction system and control method thereof and more particularly, to a jawbone distraction system and control method thereof, including a jawbone extension apparatus, a remote controller and a monitor, the jawbone distractor being configured to allow a horizontal shift of alveolar bone as well as performing vertical jawbone distraction, being precisely controlled in a wireless mode and configured to control a drive of the jawbone distractor through the remote controller while ascertaining a driving state by the monitor.

BACKGROUND ART

There are so many cases of causing deformities due to alveolar bone in malformed maxillofacial patients. For example, those can be called patients with cleft lips and palates, jutting chins, deformation, and edentulous patients arising from traumas.

In case of a child with cleft lip and palate, it has a cicatrix after an early surgical operation and therefore meets with an impediment to growth of bone to cause deformation of jawbone. As a chin is normally growing despite abnormal growth of maxilla, the circumstance around a nose becomes to be recessed (undergrowth of upper jawbone) or the chin becomes to be protruded (overgrowth of lower jawbone). For solving these troubles, it is usual to conduct a corrective surgery for maxilla and chin in the end of the season when the maxilla is growing (a teenage), which means a surgical procedure to pull an undergrown maxilla frontward so as to revive the volume of the central portion in face or push a chin backward so as to make the chin shown smaller, with which a corrective treatment for teeth is accompanied to make rows of teeth fit well each other between the top and the bottom.

With respect to a jutting chin, there may be two cases of bad and acceptable teeth engagements. The latter can be correctable by simple surgery, whereas the former is inevitable to have surgery and correction. If even a correction is not contributable to occlusion because a jutting chin is too excessive, it is necessary to perform surgery for push the whole body of jaw including teeth and alveolar, which is regarded as the greatest surgery in the cases called jutting chins. It is also necessary to perform a dental correction before and after such surgery because the surgery can not be still acceptable thereto.

In other words, it is impossible for the cleft lip and palate and the jutting chin to be with a teeth shift by way of a corrective treatment in a classic manner because of discontinuity of alveolar, from which there are generated a malocclusion with lateral disharmony of maxilla due to cicatrix tissues after surgery, and a failure of thrive of intermediate face due to a frontward undergrowth of maxilla after surgery.

As a way for remedying faces and reconstructing rows of teeth for deformed patients and edentulous patients arising from traumas, it is required to perform surgery such as alveolar bone distraction or extension for frontward and backward teeth shifts, or a corrective treatment for prosthetic restoration.

As a surgical treatment for the deformed maxillofacial patients and defective patients, for the purpose of increasing a length of chin bone in inherent and acquired deformities, it is possible to result in an appropriate face and occlusion by adjusting a direction of distraction with a cutoff position and angle of bone. To do this, jawbone distractors are needed and can be briefly classified into extra-oral and intra-oral types.

An extra-oral distractor is an apparatus that is installed out of an oral cavity and controlled at the outside of the skin, advantageous in simplicity of installation, easiness of handling, controllability of distracting direction and so on, but inconvenient for a social life and may remain a permanent scar on the face.

An intra-oral distractor is an apparatus that is installed within an oral cavity, being widely used due to the shortness of the extra-oral one. However, even the intra-oral distractor may also cause various problems involved in aesthetic view, life convenience, complication and so on because its control part is located out of the oral cavity.

With the development of medial machinery and arts, corrective treatments have been diversified through surgical operations at maxillofacial parts. Among them, a technique of bone distraction has been being used to extend horizontal and vertical lengths of maxilla and chip and broaden an arch. The horizontal bone distraction has acted as a limit to clinical application because of its structural property in the bone distractor.

In recent years, being published are the studies about influences of bone distraction to peripheral tissues during bone distraction, particularly various analyses about influences of continuous, interrupted-continuous and intermittent forces to bone distraction, but still in shortness of objective materials since it is difficult to control minute forces due to a mechanical limitation of the distractor. Furthermore, during bone distraction, the feature of bone distractor necessitating external control may cause a complication such as an inflammation and a skin cicatrix due to contagion from an external projection. Therefore, there is a need for a jawbone distractor capable of being controlled more precisely without any external projection, hence free from a complication.

Generally, bone distracters being commercialized these days are mostly related to vertical bone distraction for recovering vertically defected bones, but horizontal alveolar shifters highly usable for corrective treatment region are almost not applied. Therefore, it is also required an apparatus capable of horizontally shifting an alveolar bone as well as performing vertical bone distraction.

In regard to the current technology of bone distraction, there are accompanied with limitations and complications such that an inadequate distraction force may be applied to a reviving tissue to generate a newly deformed bone, a direction of distraction may be set due to a failure of setting a treatment plan, an error for a surgical process, and a misuse of an apparatus, and excessive distraction of soft tissues may cause damage to peripheral soft tissues.

Therefore, the present invention provides a jawbone distraction system capable of horizontally shifting an alveolar as well as allowing vertical bone distraction, being precisely controlled in a wires mode and free from a complication without any outward projection.

DISCLOSURE

Technical Problem

The present invention is directed to provide a system and control method for jawbone distraction, which is capable of horizontally shifting an alveolar bone as well as allowing vertical bone distraction, being configured to permit a precise wireless control thereto and control drive with a remote controller while ascertaining a driving state thereof by way of a monitor.

Technical Solution

To solve the technical problem, according to the present invention, a jawbone distraction system, including a micro-actuator and an actuator controller controlling the micro-actuator, being formed to include a jawbone distractor installed to an upper bone and a lower bone connected to the upper bone and configured to adjust an interval between the upper and lower bones, and a monitor generating and wirelessly transmitting an actuator control signal to the jawbone distractor, may further include: a remote controller including a forward shift key and a reverse shift key that set the micro-actuator to shift each in a forward direction and a reverse direction, in which the monitor may be configured to include an arithmetic processor generating an actuator control signal in response to a forward shift key signal and a reverse shift key signal that are received from the remote controller.

Further according to the present invention, a jawbone distraction system may include a micro-actuator and an actuator controller controlling the micro-actuator, being formed to include a jawbone distractor installed to an upper bone and a lower bone connected to the upper bone and configured to adjust an interval between the upper and lower bones, and a monitor generating and wirelessly transmitting an actuator control signal to the jawbone distractor, in which the monitor may be configured to include: a key input unit including a forward shift key and a reverse shift key that set the micro-actuator to be shifted each in a forward direction and a reverse direction; and an arithmetic processor generating an actuator control signal in response to a forward shift key signal and a reverse shift key signal that are received from the key input unit.

The actuator controller may include: an actuator microcontroller wirelessly receiving the actuator control signal from the arithmetic processor; an actuator driver driving the micro-actuator in response to the actuator control signal that is received by the actuator microcontroller; and an actuator state detector detecting a voltage of a device serially coupled to the micro-actuator or a current signal of an input node of the micro-actuator as a state detection signal.

Further according to the present invention, a jawbone distraction system, including a micro-actuator and an actuator controller controlling the micro-actuator, including a jawbone distractor installed to an upper bone and a lower bone connected to the upper bone and configured to adjust an interval between the upper and lower bones, may further include: a remote controller including a forward shift key and a reverse shift key that set the micro-actuator to shift each in a forward direction and a reverse direction, in which the actuator controller may be configured to include: an actuator microcontroller generating an actuator control signal in response to a forward shift key signal and a reverse shift key signal that are received from the remote controller; and an actuator driver driving the micro-actuator in response to the actuator control signal that is received by the actuator microcontroller.

The actuator controller may further include a shift detection sensor detecting a shift distance of a lower bone support of the jawbone distractor.

The monitor may be configured to display an image, where is shifted the lower bone support of the jawbone distractor, in an X-ray image in response to a shift distance detection signal that is wirelessly received from the actuator controller.

An interface of the actuator controller and the monitor may use RS-232C, the micro-actuator may be a supersonic motor using a piezoelectric ceramic, and the micro-actuator may be controlled by a mode of PWM (Pulse Width Modulation).

The jawbone distractor may include: a lower bone support comprising an actuator installation unit fixedly installing the micro-actuator at the center and installed in a lower bone; an upper bone support installed in an upper bone connected to the lower bone and comprising a nut portion, into which a shaft having a bolt portion of the micro-actuator is inserted, at the center; and a support rod fixed to both left and right sides of the upper bone support and penetrating left and right sides of the lower bone support.

The upper bone support may include an upper bone connector including a fixing hole for helping installation in the upper bone, in which the lower bone support comprises a lower bone connector including a fixing hole for helping installation in the lower bone, and a support rod passing a support rod passage hole of the lower bone support may be configured to pass both left and right holes of a support rod fixer located at the end of the lower bone support.

The micro-actuator may include a shaft with screw threads, the shaft being configured to shift upward and downward while rotating, and the actuator controller may be located under the actuator installation unit of the lower bone support and over a support rod fixer.

The micro-actuator may be formed of a piezoelectric ceramic pillar and a shaft, wherein the shaft is located at the center of the piezoelectric ceramic pillar, wherein the shaft comprises screw threads and is configured to shift up and down while rotating, wherein the piezoelectric ceramic pillar comprises a cover enclosing the outside, wherein an outer side of the cover is connected to a signal transfer line.

Further according to the present invention, a method for driving a jawbone distraction system configured to include a jawbone distractor, a remote controller and a monitor, may include: an initializing step setting a motor step, a shift distance interval and a shift time period in the monitor and resetting (clearing) a counter; a power factor clear step setting a power factor to '0'; an interrupt enable step making an interrupt flag of a microcontroller of the jawbone distractor to be enabled; a key input determination step determining whether a key has been input into a key input unit; an interrupt flag disable determination step determining whether the interrupt flag is disabled if the key has been input into the key input unit in the key input determination step and returning to the interrupt enable step if the interrupt flag is disabled; a pulse on-time determination step determining whether a pulse on-time is '0' if the interrupt flag is not disabled in the interrupt flag disable determination step and returning to the power factor clear step if the pulse on-time is '0'; a counter value determination step reading and comparing a counter value with the pulse on-time and one period (total time) unless the pulse on-time is '0' in the pulse on-time determination step; and a pulse on-time < counter value ≤ one period step determining whether a stop mode is present if the counter value is larger than the pulse on-time but smaller than the one period (total time) in the counter value determination step, setting the power factor to be a preset minimum power factor value unless the stop mode is present, an actuator controller stopping actuator control, reducing a stored power factor value by one and returning to the power factor clear step.

The method for driving a jawbone distraction system may further include: a none-key input processing step resetting the counter unless the key has been input into the key input unit in the key input determination step, determining whether the stop mode is present, storing the power factor as a preset minimum power factor value unless the stop mode is present, the actuator controller stopping the actuator control, and reducing the stored power factor value by one; and a power factor determination step determining whether the stored power factor value is '0' after the non-key input processing step, being terminated if the power factor value is '0' and returning to the power factor clear step unless the power factor value is '0'.

The method for driving a jawbone distraction system may further include: a step of a counter value > one period or a counter value ≤ pulse, resetting the counter if the counter value is larger than the one period in the counter value determination step, determining whether a start mode is present, storing the power factor as a preset maximum power factor value if the start mode is present, increasing the stored power factor value by one, the actuator controller beginning (on) the actuator control, and returning to the power factor clear step.

Further according to the present invention, a method for driving a jawbone distraction system configured to include a jawbone distractor, a remote controller and a monitor, may include: an X-ray image loading step reading a preliminarily stored X-ray image by an arithmetic processor of the monitor; a shifter setting step setting a shifter, in which a lower bone support is installed, in the X-ray image in the arithmetic processor of the monitor; a normal operation determination step determining whether a normal state is present by comparing a preliminarily stored reference signal with an actuator state detection signal, which is received from the jawbone distractor, in the arithmetic processor of the monitor, and terminating with outputting an alert to inform abnormality unless the normal state is present; a shift detection signal reception step receiving a shift detection signal from the jawbone distractor by the arithmetic processor of the monitor if the normal state determination step determines that the normal state is present; and a shifter shifting step outputting an image, on which a shifter in which a lower bone support is installed is shifting according to a shift detection signal, in the X-ray image.

The method for driving a jawbone distraction system may further include: a jawbone distractor drive end determination step determining whether the jawbone distractor is stopped, from an actuator control signal that is generated from the arithmetic processor of the monitor, or from the actuator state detection signal or the shift detection signal that are received from the jawbone distractor, in the arithmetic processor of the monitor, terminating the arithmetic processor of the monitor if the jawbone distractor is stopped, and returning to the normal operation determination step unless the jawbone distractor is stopped.

Advantageous Effects

According to a system and control method for jawbone distraction, a jawbone distractor is capable of horizontally shifting an alveolar bone as well as allowing vertical bone distraction, being configured to permit a precise wireless control thereto and control drive with a remote controller while ascertaining a driving state thereof by way of a monitor. Thus it is possible for the jawbone distractor to be controlled wirelessly and automatically in precision without outward projection, so that there is no anxiety for complication.

While a bone distractor of the related art is exposed at the outside, penetrating the skin, a jawbone distractor of the jawbone distraction system according to the present invention, i.e. Micro-Actuator-Generated Distractor (MAGD), is installable completely within an oral cavity and workable by a remote controller, without revision surgery for driving the jawbone distractor, having an aesthetic merit even after surgery.

While a bone distractor of the related art is enabled with bone distraction through direct actuation one or two times a day by a patient guardian, a jawbone distraction system of the present invention uses an MAGD to execute remote control with more easiness and simplicity, offering manipulation and convenience.

A jawbone distraction system according to the present invention is workable with distraction/compression of jawbone and with cyclic tensile strain, capable of granting a continuous force as well as an intermittent force.

A jawbone distraction system of the present invention is capable of allowing bone distraction in the unit of micrometer, having excellent precision, reducing the possibility of contagion, i.e. a compliment, from an external wound because there is no part exposed outward.

Moreover, a jawbone distraction system can be controlled wirelessly, providing basic information for developing intra-mouth micro-actuator driven bone distractors suitable for Koreans. For instance, exact measurement values taken from analyzing radiographs and practical anatomy with Koreans can be used as outlined design materials for developing bone distracters with micro-actuators, by which jawbone distracters suitable for Koreans can be manufactured.

A jawbone distraction system of the present invention is advantageous, for clinical application, in reducing side effects after treatment and improving recuperation after surgery, lightening social expenses caused from medical and legal disputes due to aftereffects, and saving medical payments of patients.

Especially, a jawbone distraction system of the present invention is convenient in use and controllable with high precision and accuracy.

BEST MODE

Hereinafter will be described a jawbone distraction system and a control method thereof with reference to the accompanying drawings.

Figure 1:
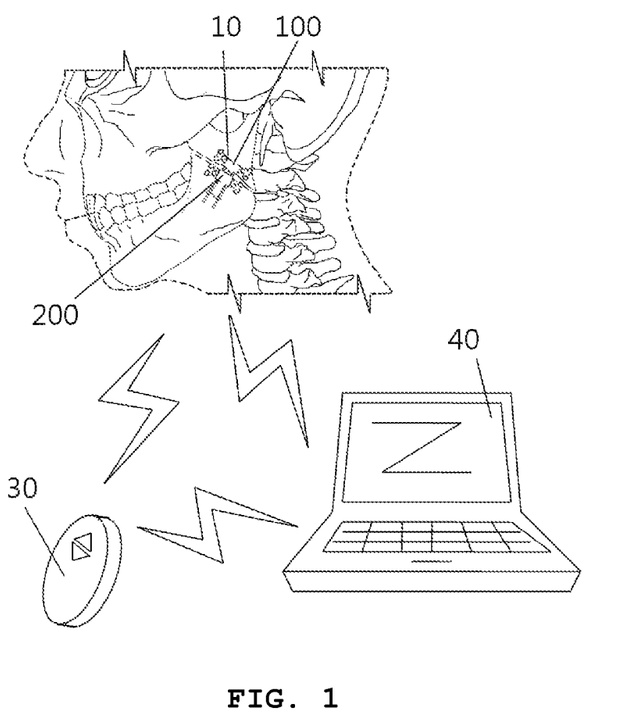
FIG. 1 is a schematic illustrating a jawbone distraction system of the present invention.

FIG. 1 is a schematic illustrating a jawbone distraction system of the present invention, including a jawbone distractor 10, a bone distraction monitor 20, and a remote controller 30, in which the remote controller 30 may be omitted.

The jawbone distractor 10 is composed of an upper bone support 100 and a lower bone support 200, acting means for separating (isolating) or combining an upper bone to which the upper bone support 100 is installed, and a lower bone to which the lower bone support 200 is installed. That is, in the jawbone distractor 10, the upper bone support 100 is installed under the ear of the upper jawbone, the lower bone support 200 is installed at the lower jawbone, connected with the upper jawbone, an actuator control signal transferred by the bone distraction monitor 20 or the remote controller 30 which is located at the outside is received at an actuator controller 350 to generate an actuator drive signal for controlling a micro-actuator 300 to be driven. Then, the micro-actuator 300 functions to separate (isolate) in a predetermined interval, or combine the upper jawbone to which the upper bone support 100 is installed, and the lower jawbone to which the lower bone support 200 is installed.

Although FIG. 1 shows an example that the jawbone distractor 10 is set between the upper jawbone and the lower jawbone which is connected with the upper jawbone, the jawbone distraction system of the present invention may not be limited thereto in implementation and rather applicable to various modes of bone distraction such as alveolar bone.

The bone distraction monitor 20 functions to generate the actuator control signal through an arithmetic process with a degree of isolation between the upper and lower bones and then wirelessly transmits the actuator control signal to the jawbone distractor 10.

According to circumstances, the bone distraction monitor 20 can also display an image signal (e.g. supersonic image signal, X-ray image signal) which is transferred by taking a picture of installation state of the jawbone distractor 10 of a patient from image devices.

The jawbone distractor 10 receives the actuator control signal from the bone distraction monitor 20 or the wireless remote controller 30 and then generates the actuator drive signal to control the micro-actuator 300 to be driven, making the upper and lower bones keep in isolation with a predetermined interval. The jawbone distractor 10 also wirelessly transmits information about a driving state of the micro-actuator 300 and an isolation state of the upper and lower bones, toward the bone distraction monitor 20.

The remote controller 30 is a remote controller to enhance the mobility of doctor, partly including a function of the bone distraction monitor, which may be omitted in case. The remote controller 30 generates the actuator control signal from arithmetic process with a degree of isolation between the upper and lower bones, and wirelessly transmits the actuator control signal to the jawbone distractor 10 and the bone distraction monitor 20.

Figure 2:
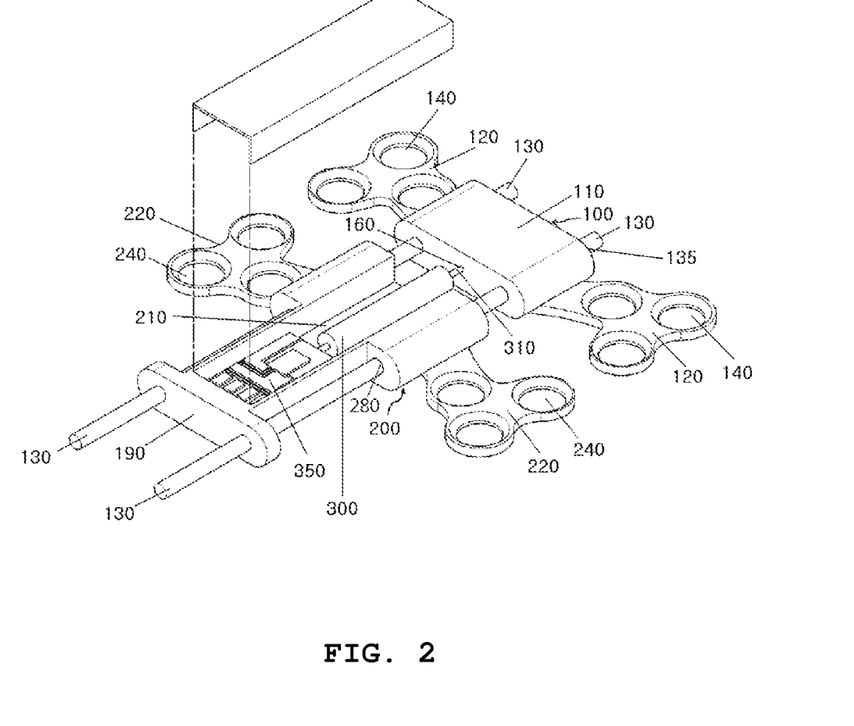
FIG. 2 is a schematic illustrating appearances of a jawbone distractor according to an embodiment of the present invention.

FIG. 2 is a schematic illustrating appearances of a jawbone distractor according to an embodiment of the present invention, including the upper bone support 100, the lower lone support 200, a support rod 130, a support rod fixer 190, the micro-actuator 300, and the actuator controller 350.

The upper bone support 100 is a support to be installed at the upper bone, being formed of an actuator insertion unit 110 and an upper bone connector 120.

The actuator insertion unit 110 is means for inserting the micro-actuator 300 into the center of the upper bone support 100, including the upper bone connector 120 at the outer left and right sides. The actuator insertion unit 110 is fixedly installed the support rods 130 by combination between bolts, which are formed at one ends of the support rods 130 at the inner left and right sides, and nuts of support rod fixing holes 135. The actuator insertion unit 110 has a nut portion 160 in the center. Into the nut portion 160 is inserted a bolt portion 310 of a shaft of the micro-actuator 300.

The upper bone connector 120 is means for installing the upper bone support 100 at the upper bone. The upper bone connector 120 includes a fixing hole 140 for settling a fixing tool such as screw.

The lower bone support 200 is a support installed at the lower bone, which is formed of an actuator installation unit 210 and a lower bone connecter 220.

The actuator installation unit 210 is means for fixedly installing the micro-actuator 300 at the center of the lower bone support 200, including the lower bone connector 220 at the outer left and right sides. In the actuator installation unit 210, the support rod 130 passes support rod passage holes 280 at the inner left and right sides and the micro-actuator 300 is fixedly installed at the center.

The lower bone connector 220 is means for installing the lower bone support 200 at the lower bone, including fixing holes 240 for installing fixing tools such as screws.

The support rods 130 formed of two members are means acting as guide rails for the lower bone support 200 to which the micro-actuator 300 is installed, which are fixedly installed at the inner left and right sides of the actuator insertion unit 110 of the upper bone support 100, passing the support rod passage holes 280 at the inner left and right sides of the actuator installation unit 210 of the lower bone support 200, and separately fixed each other by the support rod fixer 190.

The support rod fixer 190 is means for fixing one ends of the support rods 130 in a certain interval. Occasionally, the support rod fixer 190 may be integrated with the lower bone support 200.

The micro-actuator 300 is an actuator movable upward and downward while its shaft having screw threads is rotating, which is settled at the actuator installation unit 210 of the lower bone support 200 and whose shaft is inserted into the nut portion 160 of the actuator insertion unit 110 of the upper bone support 100. The micro-actuator 300 may be made up of a supersonic motor using piezoelectric ceramic.

The actuator controller 350 is means equipped with a circuit for controlling and driving the micro-actuator 300, which is located, at a position not disturbing drive of the micro-actuator 300, under the actuator installation unit 210 of the lower bone support 200 and over the support rod fixer 190. The actuator controller 350 receives the actuator control signal which is transmitted by the bone distraction monitor 20 or the wireless remote controller 30 which is located at the outside, and then generates the actuator drive signal to control the micro-actuator 300 to be driven. Additionally, the actuator controller 350 wirelessly transmits information about a current driving state of the micro-actuator 300 and an isolation state between the upper and lower bones toward the bone distraction monitor 20.

Figure 3:
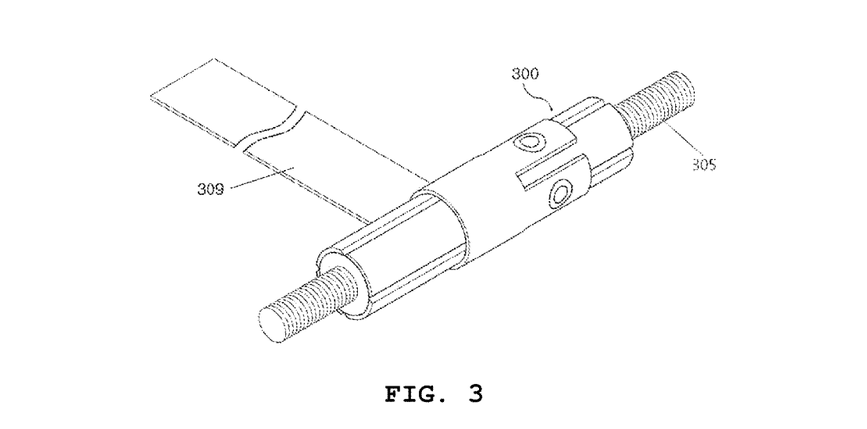
FIG. 3 illustrates an example of a micro-actuator according to an embodiment of the present invention.

FIG. 3 illustrates an example of a micro-actuator according to an embodiment of the present invention.

The micro-actuator 300 of FIG. 3 includes a piezoelectric ceramic pillar and a shaft.

The shaft is located at the center of the piezoelectric ceramic pillar, including screw threads, and configured to move up and down while rotating. The piezoelectric ceramic pillar includes a cover enclosing its outside. To an outside of the cover is connected a signal transfer line 309.

The micro-actuator 300 may be used with a supersonic motor employing a piezoelectric ceramic and configured to make the shaft, which has male screw threads, move up and down while rotating.

Figure 4:
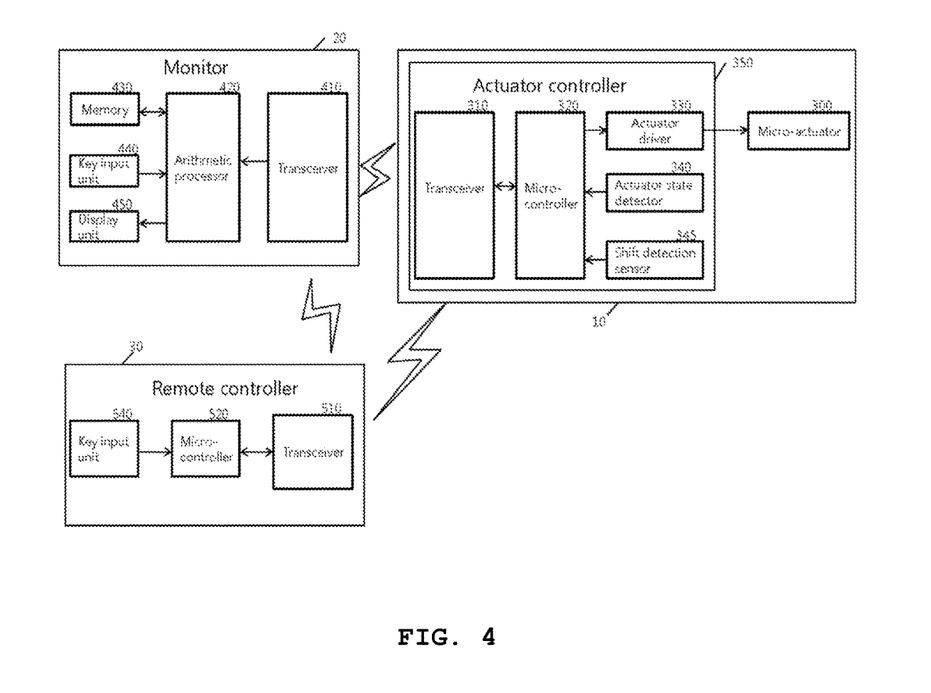
FIG. 4 is a schematic illustrating a configuration for driving a jawbone distraction system of the present invention.

FIG. 4 is a schematic illustrating a configuration for driving a jawbone distraction system of the present invention, including the jawbone distractor 10, the bone distraction monitor 20 and the remote controller 30.

The jawbone distractor 10 includes the actuator controller 350 and the micro-actuator 300, and the actuator controller 350 includes a transceiver 310, a microcontroller 320, an actuator driver 330, an actuator state detector 340 and a shift detection sensor 345.

The microcontroller 320 receives the actuator control signal from the monitor 20 or the remote controller 30 and then outputs the actuator control signal to the actuator driver 330. The microcontroller 320 receives a state detection signal of the actuator from the actuator state detector 340 and transfers the state detection signal to the monitor 20 through the transceiver 310, and transfers a shift detection signal to the monitor 20 through the transceiver 310 from the shift detection sensor 345.

Here, it is permissible to employ an I2C interface for controlling a driver IC, i.e. the microcontroller 320. The microcontroller 320 may use a host, i.e. an embedded system microcontroller that is workable in the I2C interface and the serial interface RS-232C with the monitor 20.

The actuator driver 330 functions to drive the micro-actuator 300 in response to the actuator control signal which is received from the microcontroller 320.

Figure 5:
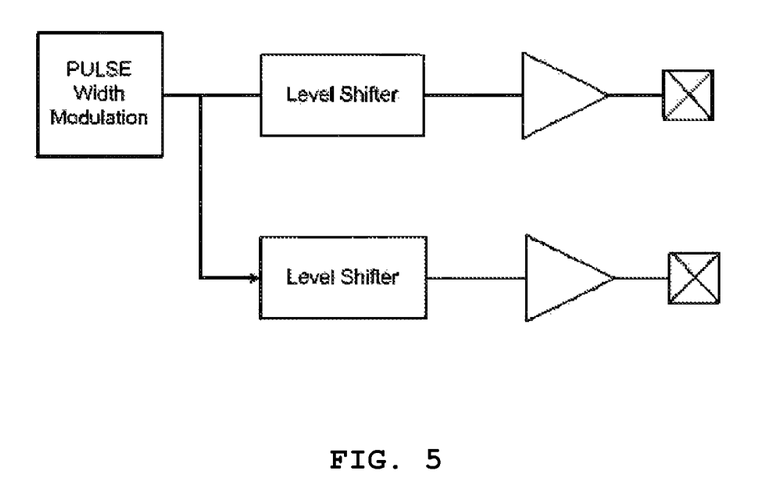
FIG. 5 is a schematic illustrating a driving feature of an actuator driver of FIG. 4.

The driver for driving the micro-actuator 300 (e.g. piezoelectric motor) of MAGD has a DC-DC step-up converter as shown in FIG. 5, driving a half bridge driver in a form of phase-shifted square wave with a supersonic frequency required by the piezoelectric motor.

The actuator state detector 300 is means for ascertaining a motion of the actuator and the actuator detection signal may be composed of a detection signal with a voltage of a device serially coupled to the micro-actuator 300 or with a current of a signal input node of the micro-actuator 300.

The shift detection sensor 345 functions to detect whether the lower bone support 200 has shifted (or detect a shift distance) and the shift detection signal which is detected is transmitted to the monitor 20 through the transceiver 310. The shift detection sensor 345 may be a photo sensor, an infrared sensor or a resistive sensor. The shift detection sensor 345 may be omitted otherwise.

Figure 6:
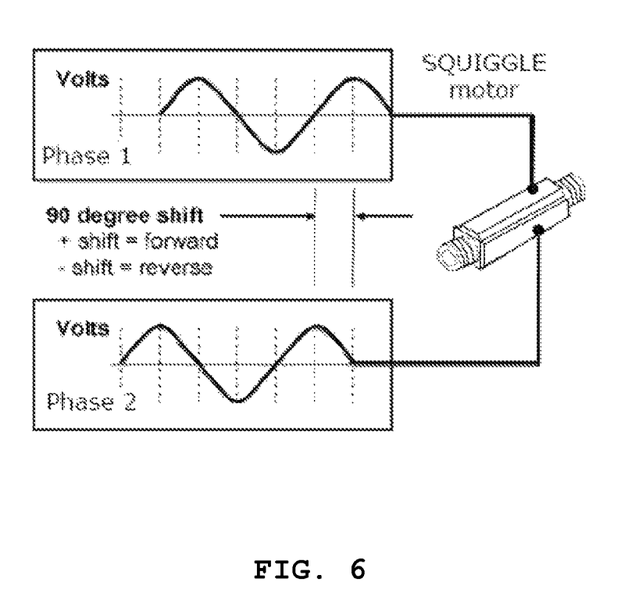
FIG. 6 is a schematic illustrating a driving mechanism of a piezoelectric motor.

The micro-actuator 300 may use an USM motor or a piezoelectric motor. A function of the piezoelectric motor can be accomplished in a circuit adjusting a velocity along a progressing direction by means of a signal period and a duty ratio according to a pulse width modulation (PWM) signal and controlling a direction by means of a phase difference between electric signals connected to a plate.

The monitor 20 is means for monitoring a driving state of the jawbone distractor 10, including a transceiver 410, an arithmetic processor 420, a memory 430, a key input unit 440 and a display unit 450.

The arithmetic processor 420 checks a driving state of the micro-actuator 300 from the actuator state detection signal which is received from the jawbone distractor 10 by way of the transceiver 410 and outputs a signal of the state signal to the display unit 450.

The arithmetic processor 420 can receive a forward or reverse drive signal from the key input unit 440, and then generate the actuator control signal and transmit the actuator control signal to the jawbone distractor 10 through the transceiver 410. The arithmetic processor 420 otherwise can receive a forward or reverse drive signal from the remote controller 30 through the transceiver 410, and then generate and transmit the actuator control signal to the jawbone distractor 10 through the transceiver 410. The actuator control signal can be generated directly from the remote controller 30, not from the arithmetic processor 420.

Additionally, the arithmetic processor 420 receives the shift detection signal through the transceiver 410 from the jawbone distractor 10, obtains a shift distance of the micro-actuator 300, and outputs a value of the shift distance to the display unit 450. The arithmetic processor 420 can otherwise output the shift detection signal to the display unit 450 to represent, on a preliminarily stored image (e.g. X-ray image), that a lower bone support connection is shifting in response to the shift detection signal. The arithmetic processor 420 can also estimate a rotation count of the motor from the actuator control signal and obtain a shift distance of the micro-actuator 300 from the rotation count of the motor.

The memory 430 stores an output of the arithmetic processor 420, i.e. the shift distance of the micro-actuator 300.

The key input unit 330 can include a shift start key, a shift end key, a forward shift key, a reverse shift key and so on.

The display unit 450 can output an output of the arithmetic processor 420, i.e. the shift distance of the micro-actuator 300, in a form of image or graph.

The remote controller 30 is means for wirelessly controlling the micro-actuator 300, including a transceiver 510, a microcontroller 520 and a key input unit 540. The remote controller 30 can directly shift the micro-actuator 300 in the forward or reverse direction, or shift the micro-actuator 300 in the forward or reverse direction by way of the monitor 20.

The key input unit 540, including the forward shift key and the reverse shift key, inputs a key to shift the micro-actuator 300 in the forward or reverse direction.

The microcontroller 520 can transmit a forward shift signal or a reverse shift signal to the monitor 20 or the jawbone distractor 10 through the transceiver 510 from the key input unit 540.

Otherwise the microcontroller 520 can generate the actuator control signal in response to the forward or reverse shift signal and then the actuator control signal to the jawbone distractor 10 through the transceiver 510.

Figure 7:
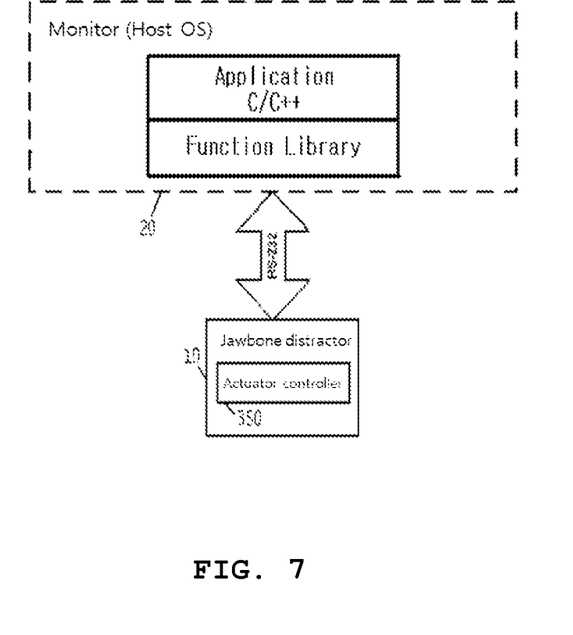
FIG. 7 is a schematic illustrating an environment of a monitor for activating a jawbone distractor of a jawbone distraction system of the present invention.

For motion control of MAGD and a wired remote control of position control command in the jawbone distraction system of the present invention, application software for host, i.e. a control program of the monitor 20, can be composed using C/C++ and API, as shown in FIG. 7, and then transfer control commands and parameters through the RS-232C serial interface.

Figure 8:
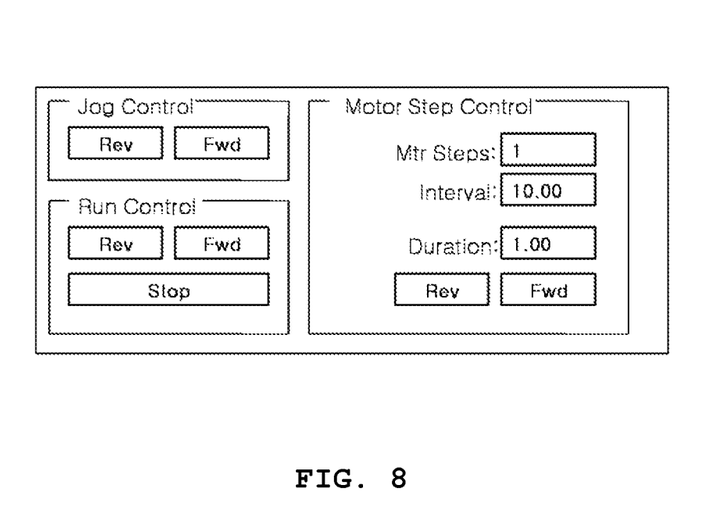
FIG. 8 illustrates an example of GUI of a monitor of a jawbone distraction system of the present invention.

As a GUI (Graphical User Interface) of a host computer for MAGD control, the monitor 20 is configured as shown in FIG. 8, capable of conducting MAGD control with numerical control by simple mouth input unit and keyboard input. With respect to the MAGD control, it is permissible to prepare three regions of JOG Control, RUN Control and STEP Control so as to accomplish each parameter control.

The JOG Control enables the MAGD to be shifted in the reverse or forward direction by clicking Rev or Fwd. Only when Rev or Fwd button is being pressed down, the MAGD shifts.

The RUN Control enables the MAGD to be shifted in the reverse or forward direction by clicking Rev or Fwd. Only when button Stop is being pressed down, the MAGD stops.

The STEP Control sets Mtr Steps (motor step), Interval (shift distance interval) and Duration (shift time period).

Into box Mtr Steps, the number of steps is input to shift the MAGD. MAGD steps are driven by a burst signal (up to 65535).

Into box Interval, a value of ms is input in correspondence with each burst interval (104 ms).

Into box Duration, a period of each burst (ms) is input. This number must be smaller than the value of Interval and may be shorter than 1 ms.

Once the step parameter of the MAGD is set, clicking Rev or Fwd can shift the MAGD in the reverse and forward direction.

In the present invention, the microcontroller 320 of the actuator controller 350 switches a Half-Bridge FET switching device, which is embedded in a drive device for controlling the micro-motor, for MGAD control, if a control parameter command is received from the monitor 20 that is a PC host computer. During this, switching rate control is performed in the manner of PWM (Pulse Width Modulation) to determine the maximum power supply time, a rotor speed and torque of the micro-motor.

Figure 9:
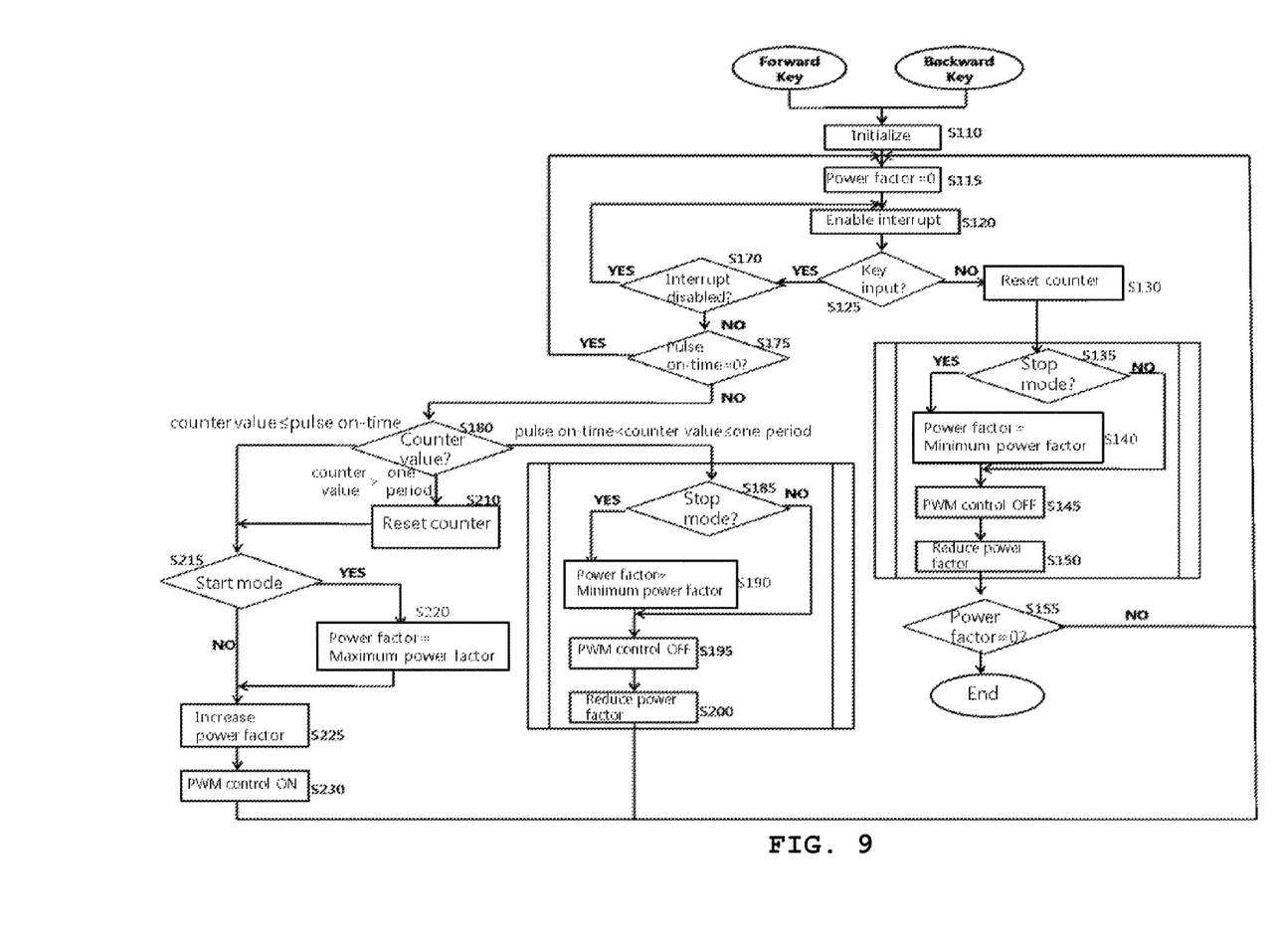
FIG. 9 is a flow chart for controlling a micro-actuator by forward and reverse direction keys in a jawbone distraction system of the present invention.

FIG. 9 is a flow chart for controlling a micro-actuator by forward and reverse direction keys in a jawbone distraction system of the present invention.

The flow chart of FIG. 9 shows the procedure of setting a period and an interval step of a PWM wave in response to a key (Distraction Key) in MAGD drive parameter control algorithms and carrying out PWM control by means of an internal counter and an interrupt.

In an initializing step, if the forward and reverse direction keys begins to be driven, Mtr Steps (motor step), Interval (shift distance interval) and Duration (shift time period) are set and the counter is reset (S110).

In a power factor clear step, a power factor goes to '0' (S115).

In an interrupt enable step, an interrupt flag of the microcontroller is forced to be set to an enable state, which makes an interrupt activated any time (S120). The interrupt enable step can wait for until the disabled interrupt flag is enabled or forcibly reset the interrupt flag.

In a key input determination step, it is determined whether a key has been input into the key input unit (S125).

In a processing step when there is no key input, if there is no key input into the key input unit, the counter is reset (S130) and then it is determined whether a stop mode is present (S135). If the stop mode is not present, a power factor is stored as a preset minimum power factor value (S140), and the actuator controller turns off the actuator control (PWM control) (S145), and reduce the stored power factor value (by one) (S150).

In a power factor determination step (namely, a determination step to find out that the power factor is '0'), it is determined whether a stored value of the power factor is '0' (S155). If the power factor value is '0', the procedure is terminated. If not, the procedure returns to the power factor clear step S115.

If a key has been applied to the key input unit in the key input determination step S125, the interrupt occurs to determine whether the interrupt flag is disabled (S170). If the interrupt flag is disabled, the procedure returns to the interrupt enable step S120.

In a pulse on-time determination step (namely, a determination step to find that a pulse on-time is '0'), it is determined whether the pulse on-time is '0' (S175). If the pulse on-time is set on '0', the procedure returns to the power factor clear step S115.

Generally, a PWM control signal is a signal formed in a pulse train with periods that repeats High and Low states, where the High state is represented as on and the Low state is represented as off.

In a counter value determination step, if the pulse on-time is not '0' at the pulse on-time determination step (S175), the counter value is read and compared to the pulse on-time and one period (total time) S180.

In a determination step of pulse on-time < counter value ≤ one period, if the counter value is found as larger than the pulse on-time and smaller than one period (total time) at the counter value determination step S180, it is determined whether the stop mode is present (S185). If not the stop mode, the power factor is set to the preset minimum power factor value (S190), the actuator controller turns off the actuator control (PWM control) (S195), the stored power factor value is reduced (by one) (S200) and the procedure returns to the power factor clear step S115.

In a determination step of a counter value > one period or a counter value ≤ pulse on-time, if the counter value is found as larger than one period (total time) at the counter value determination step S180, the counter is reset (S210) and it is determined whether the start mode is present (S215). If the start mode is present, the power factor is stored as the preset maximum power factor value (S220), the stored power factor value is increased by one (S225), the actuator controller begins (turns on) the actuator control (PWM control) (S230) and the procedure returns to the power factor clear step S115.

Figure 10:
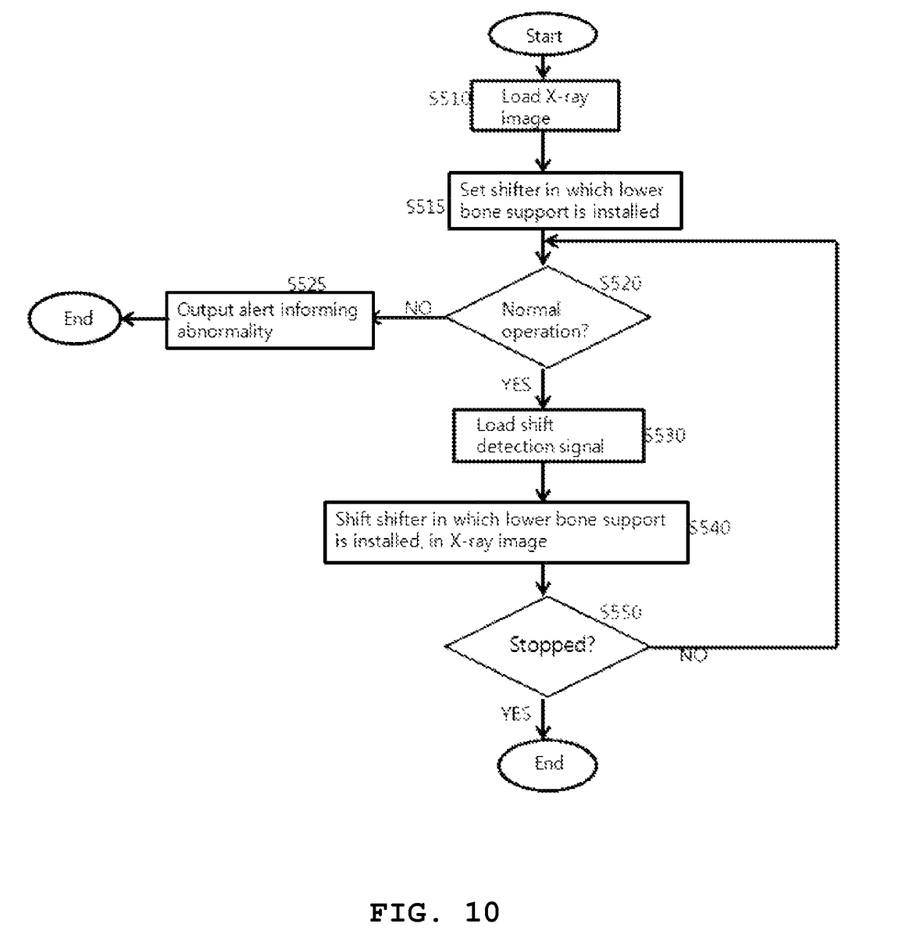
FIG. 10 shows an example of flow chart for outputting a shifted image of a jawbone distractor from a monitor of a jawbone distraction system of the present invention.

FIG. 10 shows an example of flow chart for outputting a shifted image of a jawbone distractor from a monitor of a jawbone distraction system of the present invention.

In an X-ray image loading step, the arithmetic processor 420 of the monitor 20 reads a preliminarily stored X-ray image (S510). Here, the stored X-ray image is an X-ray image after installing the jawbone distractor.

In a shifter setting step, a shifter in which the lower bone support is installed is set (S515). It is possible to automatically calculate the set of the shifter, in which the lower bone support is installed, using an image. Otherwise a value established by a user through GUI can be loaded into the arithmetic processor 420 and used therein.

In a normal operation determination step, it is determined by comparing a preliminarily stored reference signal with an actuator state detection signal that is received from the jawbone distractor 10 whether the operation of the actuator is a normal state (S520). If it is not the normal state, an alert informing an abnormal state is output to a speaker (not shown) or the display unit 450 (S525) and the procedure is terminated.

In a shift detection signal reception step, if it is found as the normal state at the normal operation determination step S520, the shift detection signal is received from the jawbone distractor (S530).

In a shifter shifting step, the shifter in which the lower bone support is installed is shifted in response to the shift detection signal on the X-ray image (S540).

In a jawbone distractor drive end determination step, whether the jawbone distractor 10 stops driving is determined by the actuator control signal generated from the arithmetic processor 420 of the monitor 20, or the actuator state detection signal or the shift detection signal received from the jawbone distractor 10 (S550). If the jawbone distractor 10 stops, the arithmetic processor of the monitor 20 is terminated thereby. If the jawbone distractor 10 is still not stopped, the procedure returns to the normal operation determination step S520.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

INDUSTRIAL APPLICABILITY

The present invention is concerned with a jawbone distraction system and a control method thereof, applicable to surgical treatments for deformed maxillofacial disorder patients and defective patients.

What is claimed is:

1. A jawbone distraction system comprising:
a jawbone distractor including
an upper bone support configured to be installed to an upper bone, and
a lower bone support configured to be installed to a lower bone;
a micro-actuator disposed on the lower bone support and configured to adjust an interval between the upper bone support and the lower bone support;
an actuator controller controlling the micro-actuator and including a shift detection sensor for detecting the interval between the upper bone support and the lower bone support;
a monitor including an arithmetic processor, a display unit and a memory, the monitor being configured to display images on the display unit, the arithmetic processor generating and wirelessly transmitting an actuator control signal to the actuator controller;
a remote controller including a forward shift key and a reverse shift key that set the micro-actuator to shift each in a forward direction and a reverse direction,
wherein the arithmetic processor reads a preliminarily stored X-ray image of the upper and lower bones which is taken after installing the jawbone distractor to the upper and lower bones, sets a portion of the preliminarily stored x-ray image in which the lower bone support is installed as a shifter, receives the interval detected by the shift detection sensor from the actuator controller and generates an X-ray image in which the shifter is shifted by the interval from the preliminarily stored X-ray image and displays the X-ray image on the display unit.

2. The jawbone distraction system according to claim 1, wherein the actuator controller further comprises:
an actuator microcontroller wirelessly receiving the actuator control signal from the arithmetic processor;
an actuator driver driving the micro-actuator in response to the actuator control signal that is received by the actuator microcontroller; and
an actuator state detector detecting a voltage of a device coupled to the micro-actuator or a current signal of an input node of the micro-actuator as a state detection signal.

3. The jawbone distraction system according to claim 1, wherein an interface of the actuator controller and the monitor uses RS-232C.

4. The jawbone distraction system according to claim 1, wherein the micro-actuator is a supersonic motor using a piezoelectric ceramic.

5. The jawbone distraction system according to claim 4, wherein the micro-actuator is controlled by a mode of PWM (Pulse Width Modulation).

6. The jawbone distraction system according to claim 1, wherein the lower bone support includes an actuator installation unit for fixedly installing the micro-actuator, and
the upper bone support includes a nut portion into which a shaft having a bolt portion of the micro-actuator is inserted.

7. The jawbone distraction system according to claim 6, wherein the jawbone distractor further comprises support rods fixed to both left and right sides of the upper bone support and penetrating left and right sides of the lower bone support.

8. The jawbone distraction system according to claim 7, wherein the upper bone support comprises an upper bone connector including a fixing hole for fixing the upper bone support, and
wherein the lower bone support comprises a lower bone connector including a fixing hole for fixing the lower bone support.

9. The jawbone distraction system according to claim 7, wherein the support rods pass support rod passage holes of the lower bone support and both left and right holes of a support rod fixer located at the end of the lower bone support.

10. The jawbone distraction system according to claim 6, wherein the actuator controller is located under the actuator installation unit of the lower bone support and over a support rod fixer.

11. The jawbone distraction system according to claim 1, wherein the micro-actuator comprises a shaft with screw threads, the shaft being configured to shift upward and downward while rotating.

12. The jawbone distraction system according to claim 11, wherein the micro-actuator is formed of a piezoelectric ceramic pillar and the shaft,
wherein the shaft is located at the center of the piezoelectric ceramic pillar,
wherein the piezoelectric ceramic pillar comprises a cover enclosing the outside, and
wherein an outer side of the cover is connected to a signal transfer line.

13. A jawbone distraction system comprising:
a jawbone distractor including
an upper bone support configured to be installed to an upper bone, and
a lower bone support configured to be installed to a lower bone;
a micro-actuator disposed on the lower bone support and configured to adjust an interval between the upper bone support and the lower bone support;

an actuator controller controlling the micro-actuator and including a shift detection sensor for detecting the interval between the upper bone support and the lower bone support;

a monitor including
- a key input unit including a forward shift key and a reverse shift key that set the micro-actuator to be shifted each in a forward direction and a reverse direction,
- a memory, and
- an arithmetic processor generating an actuator control signal in response to an input from the key input unit, the monitor being configured to display images on a display unit, wherein the arithmetic processor reads a preliminarily stored X-ray image of the upper and lower bones which is taken after installing the jawbone distractor to the upper and lower bones, sets a portion of the preliminarily stored x-ray image in which the lower bone support is installed as a shifter, receives the interval detected by the shift detection sensor from the actuator controller and generates an X-ray image in which the shifter is shifted by the interval from the preliminarily stored X-ray image and displays the X-ray image on the display unit.

14. The jawbone distraction system according to claim 13, wherein the actuator controller further comprises:
- an actuator microcontroller wirelessly receiving the actuator control signal from the arithmetic processor;
- an actuator driver driving the micro-actuator in response to the actuator control signal that is received by the actuator microcontroller; and
- an actuator state detector detecting a voltage of a device coupled to the micro-actuator or a current signal of an input node of the micro-actuator as a state detection signal.

15. The jawbone distraction system according to claim 13, wherein an interface of the actuator controller and the monitor uses RS-232C.

16. The jawbone distraction system according to claim 13, wherein the micro-actuator is a supersonic motor using a piezoelectric ceramic.

17. The jawbone distraction system according to claim 13, wherein the lower bone support includes an actuator installation unit for fixedly installing the micro-actuator, and
the upper bone support includes a nut portion into which a shaft having a bolt portion of the micro-actuator is inserted.

18. A method for driving a jawbone distraction system including a jawbone distractor, a remote controller and a monitor, the method comprising:
- an initializing step setting a motor step, a shift distance interval and a shift time period in the monitor and resetting (clearing) a counter;
- a power factor clear step setting a power factor to '0';
- an interrupt enable step making an interrupt flag of the microcontroller of the jawbone distractor to be enabled;
- a key input determination step determining whether a key has been input into a key input unit;
- an interrupt flag disable determination step determining whether the interrupt flag is disabled if the key has been input into the key input unit in the key input determination step and returning to the interrupt enable step if the interrupt flag is disabled;
- a pulse on-time determination step determining whether a pulse on-time is '0' if the interrupt flag is not disabled in the interrupt flag disable determination step and returning to the power factor clear step if the pulse on-time is '0';
- a counter value determination step reading and comparing a counter value with the pulse on-time and one period (total time) unless the pulse on-time is '0' in the pulse on-time determination step; and
- a pulse on-time < counter value ≤ one period step determining whether a stop mode is present if the counter value is larger than the pulse on-time but smaller than the one period (total time) in the counter value determination step, setting the power factor to be a preset minimum power factor value unless the stop mode is present, an actuator controller stopping actuator control, reducing a stored power factor value by one and returning to the power factor clear step.

19. The method according to claim 18, further comprising:
- a none-key input processing step resetting the counter unless the key has been input into the key input unit in the key input determination step, determining whether the stop mode is present, storing the power factor as a preset minimum power factor value unless the stop mode is present, the actuator controller stopping the actuator control, and reducing the stored power factor value by one; and
- a power factor determination step determining whether the stored power factor value is '0' after the non-key input processing step, being terminated if the power factor value is '0' and returning to the power factor clear step unless the power factor value is '0'.

20. The method according to claim 19, further comprising:
- a determination step of a counter value > one period or a counter value ≤ pulse on-time, resetting the counter if the counter value is larger than the one period in the counter value determination step, determining whether a start mode is present, storing the power factor as a preset maximum power factor value if the start mode is present, increasing the stored power factor value by one, the actuator controller beginning the actuator control, and returning to the power factor clear step.

21. The method according to claim 18, further comprising:
- a determination step of a counter value > one period or a counter value ≤ pulse on-time, resetting the counter if the counter value is larger than the one period in the counter value determination step, determining whether a start mode is present, storing the power factor as a preset maximum power factor value if the start mode is present, increasing the stored power factor value by one, the actuator controller beginning the actuator control, and returning to the power factor clear step.

22. A method for driving a jawbone distraction system including a jawbone distractor, a remote controller and a monitor, the method comprising:
- an X-ray image loading step reading a preliminarily stored X-ray image by an arithmetic processor of the monitor;
- a shifter setting step setting a shifter, in which a lower bone support is installed, in the X-ray image in the arithmetic processor of the monitor;
- a normal operation determination step determining whether a normal state is present by comparing a preliminarily stored reference signal with an actuator state detection signal, which is received from the jawbone distractor, in the arithmetic processor of the monitor, and terminating with outputting an alert to inform abnormality unless the normal state is present;
a shift detection signal reception step receiving a shift detection signal from the jawbone distractor by the arithmetic processor of the monitor if the normal state determination step determines that the normal state is present; and
a shifter shifting step outputting an image, on which a shifter in which a lower bone support is installed is shifting according to a shift detection signal, in the X-ray image.

23. The method according to claim 22, further comprising:
a jawbone distractor drive end determination step determining whether the jawbone distractor is stopped, from an actuator control signal that is generated from the arithmetic processor of the monitor, or from the actuator state detection signal or the shift detection signal that are received from the jawbone distractor, in the arithmetic processor of the monitor, terminating the arithmetic processor of the monitor if the jawbone distractor is stopped, and returning to the normal operation determination step unless the jawbone distractor is stopped.

24. A jawbone distraction system comprising:
a jawbone distractor including
an upper bone support configured to be installed to an upper bone and including
a nut portion formed in a center of the upper bone support,
support rod fixing holes formed in both sides of the nut portion, and
upper bone connectors extending outwardly from both sides of the upper bone support for fixing the upper bone support, each of the upper bone connector having a planar shape and including a plurality of fixing holes therein,
a lower bone support configured to be installed to a lower bone and having
an actuator installation unit installed at a center portion of the lower bone support,
a support rod fixer disposed at an end of the lower bone support,
support rod passage holes formed in both sides of the actuator installation unit, and
lower bone connectors extending outwardly from both sides of the lower bone support for fixing the lower bone support, each of the lower bone connector having a planar shape and including a plurality of fixing holes therein;
a micro-actuator disposed on the actuator installation unit of the lower bone support and configured to adjust an interval between the upper bone support and the lower bone support;
an actuator controller controlling the micro-actuator;
a monitor generating and wirelessly transmitting an actuator control signal to the actuator controller and displaying a image or data.

25. The jawbone distraction system according to claim 24, wherein the actuator controller further comprises at least one of:
a shift detection sensor for detecting the interval between the upper bone support and the lower bone support;
an actuator state detector detecting a voltage of a device coupled to the micro-actuator or a current signal of an input node of the micro-actuator as a state detection signal.

26. The jawbone distraction system according to claim 24, wherein the micro-actuator is a supersonic motor using a piezoelectric ceramic.

27. The jawbone distraction system according to claim 26, wherein the ultra sonic motor is formed of a piezoelectric ceramic pillar,
the piezoelectric ceramic pillar comprises a cover enclosing the outside, and
an outer side of the cover is connected to a signal transfer line.

28. The jawbone distraction system according to claim 24, wherein the jawbone distractor further comprises at least one support rod of which a first end is inserted into the support rod fixing holes of the upper bone support and a second end is inserted into the support rod passage holes of the lower bone support.

29. The jawbone distraction system according to claim 24, wherein the micro-actuator comprises a shaft with screw threads in both sides thereof, the screw threads of a first side is coupled to the nut portion of the supper bone support.

* * * * *